US008637476B2

(12) United States Patent
Li et al.

(10) Patent No.: US 8,637,476 B2
(45) Date of Patent: Jan. 28, 2014

(54) APOPTOTIC CELL-MEDIATED TRANSFECTION OF MAMMALIAN CELLS WITH INTERFERING RNA

(75) Inventors: Fengchun Li, Loma Linda, CA (US); Alan P. Escher, Redlands, CA (US)

(73) Assignee: Loma Linda University, Loma Linda, CA (US)

( * ) Notice: Subject to any disclaimer, the term of this patent is extended or adjusted under 35 U.S.C. 154(b) by 435 days.

(21) Appl. No.: 12/440,912

(22) PCT Filed: Sep. 28, 2007

(86) PCT No.: PCT/US2007/079876
§ 371 (c)(1),
(2), (4) Date: Mar. 11, 2009

(87) PCT Pub. No.: WO2008/039980
PCT Pub. Date: Apr. 3, 2008

(65) Prior Publication Data
US 2010/0068813 A1    Mar. 18, 2010

Related U.S. Application Data

(60) Provisional application No. 60/827,343, filed on Sep. 28, 2006.

(51) Int. Cl.
*C12N 15/11*    (2006.01)
(52) U.S. Cl.
USPC ........................................................ 514/44 A
(58) Field of Classification Search
USPC ........................................................ 514/44 A
See application file for complete search history.

(56) References Cited

U.S. PATENT DOCUMENTS

| | | | |
|---|---|---|---|
| 6,410,273 | B1 | 6/2002 | Crouzet et al. |
| 6,602,709 | B1 | 8/2003 | Albert et al. |
| 2002/0031521 | A1 | 3/2002 | Spetz-Holmgren et al. |
| 2003/0176378 | A1 | 9/2003 | Weiner et al. |
| 2005/0214945 | A1* | 9/2005 | Semmes, IV et al. ........ 435/456 |
| 2006/0153842 | A1 | 7/2006 | Lake et al. |
| 2007/0093440 | A1* | 4/2007 | Champion et al. .............. 514/44 |
| 2008/0194510 | A1 | 8/2008 | Escher et al. |
| 2009/0191218 | A1 | 7/2009 | Li et al. |
| 2012/0308577 | A1 | 12/2012 | Li et al. |

FOREIGN PATENT DOCUMENTS

| | | | |
|---|---|---|---|
| WO | WO 94/23050 | A1 | 10/1994 |
| WO | WO99/42564 | * | 8/1999 |
| WO | WO-99/44644 | A1 | 9/1999 |
| WO | WO-00/59538 | A2 | 10/2000 |
| WO | WO-2004/034966 | A2 | 4/2004 |
| WO | 2005121369 | A2 | 12/2005 |

OTHER PUBLICATIONS

Bergsmedh A. et al., "Horizontal Transfer of Oncogenes by Uptake of Apoptotic Bodies," Proceedings of the National Academy of Sciences of the United States of America 20010522 US, vol. 98, No. 11, May 5, 2001, pp. 6407-6411.
Brignone C. et al., "A Post-Ubiquitination Role for MDM2 and hHR23A in the P53 Degradation Pathway," Oncogene 20040520 GB, vol. 23, No. 23, May 20, 2004, pp. 4121-4129.
Hill J. A. et al., "Immune Modulation by Silencing IL-12 Production in Dendritic Cells Using Small Interfering RNA," Journal of Immunology 20030715 US, vol. 171, No. 2, Jul. 15, 2003, pp. 691-696.
Holmgren L. et al., "Horizontal Transfer of 1-18 DNA by the Uptake of Apoptotic Bodies," Blood 19990601 US, vol. 93, No. 11, Jun. 1, 1999, pp. 3956-3963.
Kim T. W. et al., "Modification of Professional Antigen-Presenting Cells With Small Interfering RNA in Vivo to Enhance Cancer Vaccine Potency," Cancer Research 20050101 US, vol. 65, No. 1, Jan. 1, 2005, pp. 309-316.
Li A. et al., "Saving Death: Apoptosis for Intervention in Transplantation and Autoimmunity," Clinical & Developmental Immunology, vol. 13, No. 2-4, Jun. 2006, pp. 273-282.
Li M. et al., "Induction of RNA Interference in Dendritic Cells," Immunologic Research 2004 US, vol. 30, No. 2, 2004, pp. 215-230.
Liu G. et al., "Phagocytosis of Apoptotic Cells and Immune Regulation," Scandinavian Journal of Immunology 200607 GB, vol. 64, No. 1, Jul. 2006, pp. 1-9.
Liu G. et al., "Small Interference RNA Modulation of IL-10 in Human Monocyte-Derived Dendritic Cells Enhances the Th1 Response," European Journal of Immunology 200406 DE, vol. 34, No. 6, Jun. 2004, pp. 1680-1687.
Papoutsaki M. et al., "The P73 Gene is an Anti-Tumoral Target of the RAR[beta]/[gamma]-selective Retinoid Tazarotene," Journal of Investigative Dermatology 200412 US, vol. 123, No. 6, Dec. 2004, pp. 1162-1168.
Subramanian T. et al., "Pro-Apoptotic Activity of Transiently Expressed BCL-2 Occurs Independent of BAX and BAK," Journal of Cellular Biochemistry 20030815 US, vol. 89, No. 6, Aug. 15, 2003, pp. 1102-1114.
Extended European Search Report for related European Patent Application No. 07843470.1, Loma Linda University, Jan. 21, 2010, 10 pages.
Loma Linda University et al., Office Action dated Mar. 2, 2011 issued in related European Patent Application No. 07843470.1.
Machida K. et al., "Suppression of Apoptosis by Cyclophilin D via Stabilization of Hexokinase II Mitochondrial Binding in Cancer Cells," The Journal of Biological Chemistry, May 19, 2006, vol. 281, No. 20, May 19, 2006 pp. 14314-14320.

(Continued)

*Primary Examiner* — Brian Whiteman
(74) *Attorney, Agent, or Firm* — McDermott Will & Emery LLP

(57) ABSTRACT

Mammalian host cells for use in a cell-mediated tranfection process, which contain an RNAi molecule and an expression vector for a pro-apoptotic protein. The method includes inducing apoptotic cell (AC) death in mammalian cells that contain an RNAi molecule capable of downregulating a chosen target gene. Living cells expressing the target gene are then exposed to the ACs. The ACs are processed by the living cells, and the RNAi molecule in the ACs downregulates the expression of the target gene in living cells.

25 Claims, 3 Drawing Sheets

(56) References Cited

OTHER PUBLICATIONS

Geng-Feng et al., Cancer Biology & Therapy, 2005 vol. 4, No. 8, pp. 822-829, see especially Abstract, p. 823 and Figure 4.
Tao et al., British Journal of Dermatology, 2005 vol. 153, pp. 715-724, see especially Abstract, p. 716, and Figure 5.
Zhang et al., Breast Cancer Research and Treatment, 2005 vol. 96, pp. 267-277, see especially Abstract, p. 269 and Figures 4-6.
Li et al., International Search Report and Written Opinion of the International Searching Authority issued in parent International Patent Application No. PCT/US07/79876 on Nov. 3, 2008.
Scanlon, K.J., "Anti-Genes: siRNA, Ribozyme and Antisense," Current Pharmaceutical Biotechnology, 2004, vol. 5, pp. 415-420 (6 pages).
International Preliminary Report on Patentability dated Nov. 13, 2009 issued in parent International Patent Application No. PCT/US07/79876.
Del Prete, et al., "Degradation of Cellular mRNA is a General Early Apoptosis-Induced Event," The FASEB Journal, 16:2003-2005 (2002).
Adamus, et al., "Autoimmunity against Carbonic Anhydrase II Affects Retinal Cell Functions in Autoimmune Retinopathy", J. Autoimmun. 32(2): 133-139, 2009.
Balasa, B., et al., "Vaccination with glutamic acid and decarboxylase plasmid DNA protects mice from spontaneous autoimmune diabetes and B7/CD28 costimulation circumvents that protection," Clin Immunol 99(2): 241-52, (2001).
Belakova, et al., "DNA vaccines: are they still just a powerful tool for the future?" Arch Immunol Ther Exp (Warsz) 55(6): 387-98, (2007).
Borner, C., et al. J Cell Biol 126(4):1059-68 (1994).
Bros, et al., "A newly established murine immature dendritic cell line can be differentiated into a mature state, but exerts tolerogenic function upon maturation in the presence of gluccocorticoid", Blood, vol. 109, pp. 3820-3829; (2007).
Bumgardner, et al., "Unusual patterns of alloimmunity evoked by allogeneic liver parenchymal cells", Immunol Rev. 174: 260-79, (2000).
Chao, D.T., et al., "BCL-2 family: regulators of cell death," Annu Rev Immunol, 16: 395-419, (1998).
Chattergoon, M.A., et al., "Targeted antigen delivery to antigen-presenting cells including dendritic cells by engineered Fas-mediated apoptosis." Nat Biotechnol 18(9): 974-9, (2000).
Chernysheva, A.D., et al., "T cell proliferation induced by autologous non-T cells is a response to apoptotic cells processed by dendritic cells," J. Immunol 169(3): 1241-50, (2002).
Contreras, J.L., et al., "Cytoprotection of pancreatic islets before and early after transplantation using gene therapy," Kidney International 61(1): Suppl 79-84 (2002).
Contreras, J.L., et al., "Gene transfer of the Bcl-2 gene confers cytoprotection to isolated adult porcine pancreatic islets exposed to xenoreactive antibodies and complement," Surgery, 130(2): 166-74, (2001).
Efrat, S., et al., "Adenovirus Early Region 3 (E3) Immunomodulatory Genes Decrease the Incidence of Autoimmune Diabetes in NOD Mice," Diabetes 50(5):980-4, (2001).
Erickson, et al., "Expression of carbonic anhydrase II (CA II) promoter-reporter fusion genes in multiple tissues of transenic mice does not replicate normal patterns of expression indicating complexity of CA II regulation in vivo", Biochem Genet. 33(11-12): 421-37, (1995).
Filippova, M., et al., "Effects of Plasmid DNA Injection on Cyclophosphamide-Accelerated Diabetes in NOD Mice," DNA and Cell Biology 20(3):157-81, (2001).
Fuenette, D., et al., "DNA methylation inhibits transcription of procollagen α2(1) promoters," Biochem J. (1992) 283, 699-703.
Hedstrand, et al., "The Transcription Factors SOX9 and SOX10 are Vitiligo Autoantigens in Autoimmune Polyendocrine Syndrome Type I", The Journal of Biological chemistry, 276(38): 35390-35395 (2001).
Horner, et al., "Skin tolerance: in search of the Holy Grail", European Society for Organ Transplantation 21: 101-112, 2008.
Hosoda, et al., "Detection of autoantibody against carbonic anhydrase II in various liver diseases by enzyme-linked immunosorbent assay using appropriate conditions", Clinica Chimica Acta 342: 71-81, 2004.
Huurman, et al., "Cellular Islet Autoimmunity Associates with Clinical Outcome of Islet Cell Transplantation", PLoS ONE 3(6): e2435, 2008.
Igata, et al., "Molecular Cloning and Functional Analysis of the Murine bax Gene Promoter," Gene 238 (2): 407-15 (1999).
Ilan, Y., et al., "Insertion of the adenoviral E3 region into a recombinant viral vector prevents antiviral humoral and cellular immune responses and permits long-term gene expression," Proc Natl Acad Sci USA 94:2587-92 (1997).
Iwata, et al., Anti-Type V Collagen Humoral Immunity in Lung Transplant Primary Graft Dysfunction, J. Immunol. 181(8): 5738-5747, 2008.
Kagawa, S., et al., "A binary adenoviral vector system for expressing high levels of the proapoptotic gene bax," Gene Therapy 7: 75-9 (2000).
Kerkar, et al., "Cytochrome P4502D6193-212: A New Immunodominant Epitope and Target of Virus/Self Cross-Reactivity in Liver Kidney Microsomal Autoantibody Type 1-Positive Liver Disease", J. Immunol. 170: 1481-1489 (2003).
Klinman, et al., "Contibution of CpG motifs to the immunogenicity of DNA vaccines", Journal of Immunology, vol. 158, pp. 3635-3639 (2007).
Klinman, D., et al., "Use of CpG oligodeoxynucleotides as immune adjuvants," Imm Rev 199: 201-16 (2004).
Krieg, A.M., "The role of CpG motifs in innate immunity," Curr Opin Immun 12: 35-43 (2000).
Li, A., et al., "Co-delivery of pro-apoptotic BAX with a DNA vaccine recruits dendritic cells and promotes efficacy of autoimmune diabetes prevention in mice," Vaccine 22: 1751-63, (2004).
Li, A., et al., "Pro-apoptotic DNA vaccination ameliorates new onset of autoimmune diabetes in NOD mice and induces foxp3+ regulatory T cells in vitro," Vaccine 24: 5036-46 (2006).
Li, A., et al., "DNA vaccines for transplantation", Expert Opin, Biol. Ther. 10(6): 903-915, (2010).
Li, F., et al., "Decreased insulitis and blood glucose leves after injection of GAD-transduced lymphocytes into NOD mice", Mol. Ther. 6(6): 701-9, (2002).
Lim, et al., "Cutting Edge: Direct Suppression of B Cells by CD4+CD25+ Regulatory T Cells", J/ Immunol 175: 4180-4183 (2005).
Martin, et al., "Cell to cell interaction in the immune system", Journal of Experimental Medicine, vol. 128, pp. 855-874 (1968).
Mathisen, et al., "Gene therapy in Experimental Autoimmune Encephalomyelitis," J Clin Immunol 20(5): 327-33, (2000).
McGowan et al., "Characterization of the rat carbonic anhydrase II gene structure: sequence analysis of the 5' flanking region and 3' UTR", Gene 186(2): 181-8, (1997).
Meinck, et al., "Antibodies against glutamic acid decarboxylase: prevalence in neurological diseases", J. Neurol Neurosurg Psychiatry 71: 100-103, 2001.
Miranda, et al., "DNA Methylation: The Nuts and Bolts of Repression," J. Cell Physiol 213: 384-90 (2007).
Nakao, et al., "Regulation of Transcription and Chromatin by Methyl-CpG Binding Protein MBD1," Brain Dev 23 Suppl. 1, S174-6, (2001).
Ono, et al., "Carbonic Anhydrase in the membrane of the endoplasmic reticulum of male rat liver", Proc. Natl. Acad. Sci. vol. 89, pp. 11721-11725, Dec. 1992.
Pasquini, et al., "The Effect of CpG Sequences on the B Cell Response to a Viral Glycoprotein Encoded by a Plasmid Vector," Gene Therapy 6(8): 1448-55, (1999).
Peters, et al., "The Mouse as a model for human biology: a resource guide for complex trait analysis", Nature Reviews, vol. 8, pp. 58-69, Jan. 2007.
Pierce, M.A., et al., "Adenovirus early Region 3 Antiapoptotic 10.4K, 14.5K, and 14.7K Genes Decrease the Incidence of Autoimmune Diabetes in NOD Mice," Diabetes 52: 1119-27, (2003).

(56) References Cited

OTHER PUBLICATIONS

Rabinovitch, A., et al., "Transfection of Human Pancreatic Islets with an Anti-apoptotic Gene (bcl-2) Protects B-Cells From Cytokine-Induced Destruction," Diabetes 48(6): 1223-9, (1999).

Razin, A., "CpG Methylation, Chromatin Structure and Gene Silencing—A Three-Way Connection," The EMBO Journal, 17(17): 4905-8, (1998).

Reindl, et al., "Antibodies Against the Myelin Oligodendrcyte Glycoprotein and the Myelin Basic Protein in Multiple Sclerosis and Other Neurological Diseases: A omparative Study", Brain 122: 2047-2056, (2001).

Restifo, N.P. "Building better vaccines: how apoptotic cell death can induce inflammation and activate innate and adaptive immunity," Curr Opin Immunol 12(5): 597-603, (2000).

Reyes-Sandoval, et al., "CpG Methylation of a Plasmid Vector Results in Extended Transene Product Expression by Circumventing Induction of Immune Responses", Molecular Therapy 9(2): 249-261 (2004).

Sasaki, S., et al., "Apoptosis-mediated enhancement of DNA-raised immune responses by mutant caspases," Nat Biotechnol 19(6): 543-7, (2001).

Scheule, R.K., "The role of CpG motifs in immunostimulation and gene therapy," Adv Drug Delivery Rev 44: 119-34, (2000).

Schowalter, D.B., et al., "Heterologous Expression of Adenovirus E3-gp19K in an E1a-Deleted Adenovirus Vector Inhibits MHC I Expression in Vitro, But Does Not Prolong Transgene Expression in Vivo," Gene therapy 4: 351-60 (1997).

Seetharam, et al., "Alloimmunity and Autoimmunity in Chronic Rejection", Curr Opin Organ Transplant 15(4): 531-536, (2010).

Simone, E.A., et al., "Immunologic 'Vaccination' for the Prevention of Autoimmune Diabetes (Type 1A)," Diabetes Care 22, Suppl 2: B7-B15, (1999).

Steinman, et al., "The Induction of Tolerance by Dendritic Cells That Have Captured Apoptotic Cells", J. Exp. Med. 191(3): 411-416, (2000).

Szabo, et al., "Structure and the promoter region of the mouse gene encoding the 67-kD form of glutamic acid decarboxylase", DNA Cell Boil. 15(12): 1081-91, 1996.

Taniguchi, et al., "High Prevalence of Autoantibodies Against Carbonic Anhydrase II and Lactoferrin in Type 1 Diabetes: Concept of Autoimmune Exocrinopathy and Endocrinopathy of the Pancreas", Pancreas 27(1): 26-30, 2003.

Tisch, R., et al., "Antigen-specific mediated suppression of beta cell autoimmunity by plasmid DNA vaccination," J. Immunol 166(3): 2122-32 (2001).

Tokui, M., et al., "Studies on prevention of diabetes in NOD mice by intramuscular administration of plasmid expressing GAD and IL-4," Chemical Abstracts + Indexes, American Chemical Society, Columbus, OH, USA, 25(125): 1148 (1996).

Trucco, M., et al., "Gene Therapy Strategies to Prevent Autoimmune Disorders", Current Gene Therapy 2: 31-54 (2002).

Ulmer, et al., "Gene-based vaccines: recent technical and clinical advances", Trends Mol Med. 12(5): 216-22, (2006).

Wallet, et al., "MerTK is required for apoptotic cell-induced T cell tolerance", J. Exp. Med. 205(1): 219-232 (2008).

Watson, et al., "'Pruning' of Alloreactive CD4+ T Cells Using 5- (and 6) Carboxyfluorescein Diacetate Succinimidyl Ester Prolongs Skin Allograft Survival", The Journal of Immunology, 173: 6574-6582, 2004.

Yamaguchi, et al., "The Effect of Pretreatment with Class I Major Histocompatibility Complex (MHC) Antigens on Hepatic or Cardiac Allograft Survival in the Rat", Transplant Proc. 21(3): 3355, Jun. 1989.

Zardo, et al., "Dynamic and Reversibility of Heterochromatic Gene Silencing in Human Disease," Cell Research 15(9): 679-90, (2005).

* cited by examiner

US 8,637,476 B2

APOPTOTIC CELL-MEDIATED TRANSFECTION OF MAMMALIAN CELLS WITH INTERFERING RNA

CROSS-REFERENCE TO RELATED APPLICATIONS

The present application is a national stage of International Patent Application No. PCT/US2007/079876, titled "Apoptotic cell-mediated transfection of mammalian cells with interfering RNA," filed Sep. 28, 2007 which claims the benefit of U.S. Provisional Patent Application 60/827,343 titled "Apoptotic cell-mediated transfection of mammalian cells with interfering RNA," filed Sep. 28, 2006; the contents of which are incorporated in this disclosure by reference in their entirety.

BACKGROUND

RNA interference (RNAi) is a mechanism in molecular biology where the presence of certain fragments of double-stranded RNA (dsRNA) interferes with the expression of a particular gene, which shares a homologous sequence with the dsRNA. RNAi is a gene silencing process that requires active participation of cellular machinery. Although the specific mechanism is poorly understood, it is known that the ribonuclease enzyme Dicer binds to and cleaves short double-stranded RNA molecules (dsRNA) to produce double-stranded fragments of 21-23 base pairs with two-base single-stranded overhangs on each end. The short double-stranded fragments produced by Dicer, called small interfering RNAs (siRNAs), are then separated, presumably by an enzyme with helicase activity, and integrated into a multiprotein complex called the RNA-induced silencing complex (RISC).

Synthetic siRNAs and short hairpin RNAs (shRNAs) can be designed to have identical function. Whereas, siRNA are 2 strands of complementary RNA that can be synthesized, a shRNA is encoded by DNA as a single RNA molecule that hybridize to itself with a loop at one end. The loop is then cleaved intracellularly yielding a molecule similar to a siRNA. There are thousands of RNAi sequences available that are capable of downregulating gene expression. (See, e.g. Behlke, 2006, Mol Ther vol. 13 p 644). This method has become a universally accepted means of downregulating expression of any gene in mammalian cells.

Presently, RNAi molecules are delivered via electroporation, cationic- and liposome-mediated transfection, viral delivery, and direct injection (Behlke, 2006, Mol Ther vol. 13 p 644). One group has shown that bacteria can be used to deliver RNAi molecules to mammalian cells to screen for targeting siRNA molecules (Zhao et al., 2005, Nat Methods vol 2 p 967).

Antigen-presenting cells (APCs) like dendritic cells (DCs) are a major target for manipulation of immune responses and they have been modified using RNAi (Li et al., 2004, Immu Res vol 30 p 215). However, there is no available method that permits guaranteed co-delivery of multiple antigens and RNAi molecules to the same APC.

SUMMARY

The invention utilizes apoptotic cells (ACs) for the delivery to living cells of short RNAs capable of downregulating gene expression via RNA interference (RNAi). The invention addresses the problem of delivering RNAi molecules to mammalian cells in vivo, and the ability to link presence of an already synthesized antigen(s) with an RNAi molecule as part of the same package to be delivered.

In one embodiment the invention provides a method of generating ACs containing an RNAi molecule, which includes the steps of (1) providing an RNAi molecule, such as short interfering RNA (siRNA) or a vector capable of expressing a short hairpin RNA (shRNA), directed to a target gene of interest; (2) introducing the RNAi molecule into a pre-apoptotic cells (pre-ACs), preferably by transfection; and (3) inducing apoptosis, e.g., by UV exposure or expression of a pro-apoptotic protein like BAX, to create an AC containing the RNAi molecule.

In one embodiment the RNAi molecule contains a polynucleotide sequence substantially complementary to a messenger RNA (mRNA) encoding the target gene. In a preferred embodiment the RNAi molecule comprises a double-stranded RNA (dsRNA), which contains a sense sequence corresponding a partial sequence of the target gene mRNA and an antisense sequence that is substantially complementary and capable of specifically hybridizing to a target gene mRNA In one embodiment the RNAi molecule comprises a short double-stranded RNA molecule (dsRNA) of about 19-27 base pairs. In a preferred embodiment, the RNAi molecule is a siRNA, comprising a short double-stranded RNA molecule (dsRNA) of about 19-23 base pairs, each strand having a single-stranded overhang of about two bases on one end.

In another embodiment, the RNAi molecule is provided by a vector capable of expressing a short hairpin RNA (shRNA) or a short interfering RNA (siRNA). In a preferred embodiment, the vector contains one or more than one RNA polymerase III promoter controlling transcription of the RNAi molecule.

In one embodiment, the RNAi molecule is introduced into the mammalian cell by transfection, electroporation or microinjection. In another embodiment, the RNAi molecule is introduced into the mammalian cell by delivering a DNA plasmid or viral vector encoding a short hairpin RNA (shRNA).

In one embodiment, the method includes the further step of introducing a plasmid DNA or viral expression vector containing a polynucleotide sequence encoding a pro-apoptotic protein, such as BAX protein, into the pre-apoptotic mammalian cells.

In one embodiment the RNAi molecule and the expression vector containing a polynucleotide sequence encoding a pro-apoptotic protein are both introduced into the mammalian cell, e.g. by co-transfection in vitro or by introducing the RNAi molecule and expression vector into an organ or tissue by electroporation, gene-gun, or injection.

In one embodiment, the present invention provides a method of transfecting a mammalian cell, which includes the steps of: (a) providing a mammalian cell expressing a target gene, wherein the mammalian cell is capable of phagocytosis; and (b) exposing the mammalian cell to an apoptotic cell, containing an RNAi molecule capable of downregulating the target gene, under conditions whereby the apoptotic cell is taken up by the mammalian cell. The RNAi molecule then downregulates expression of the target gene in the mammalian cell. In alternative embodiments, the mammalian cells are exposed to the apoptotic cells in vivo or in vitro. In a preferred embodiment, the mammalian cell is an antigen presenting cell.

In another embodiment, the present invention provides a mammalian host cell, comprising: (a) One or several RNAi molecules capable of downregulating a target gene; and (b) an expression vector capable of expressing a pro-apoptotic protein. In a preferred embodiment the mammalian host cell expresses one or several antigens, like autoantigens or donor antigens. Mammalian host cells in accordance with this aspect of the present invention can be converted to ACs for use in cell-mediated transfection procedures.

Many cells can process ACs, in particular, antigen presenting cells (APCs) like dendritic cells (DCs) that direct immune responses. The ability to deliver antigen and a RNAi molecule capable of modifying the function of an APC, like DC, as part of the same package will permit increased control over induced immune responses (i.e., tolerogenic vs immunogenic) for antigens present in ACs. This approach can be adapted for use in prevention of transplant rejection (with donor antigens) and treatment of autoimmune diseases (with autoantigens).

BRIEF DESCRIPTION OF THE DRAWINGS

These features, aspects and advantages of the present invention will become better understood with regard to the following description, appended claims and accompanying drawings where:

DETAILED DESCRIPTION

Figure 1:
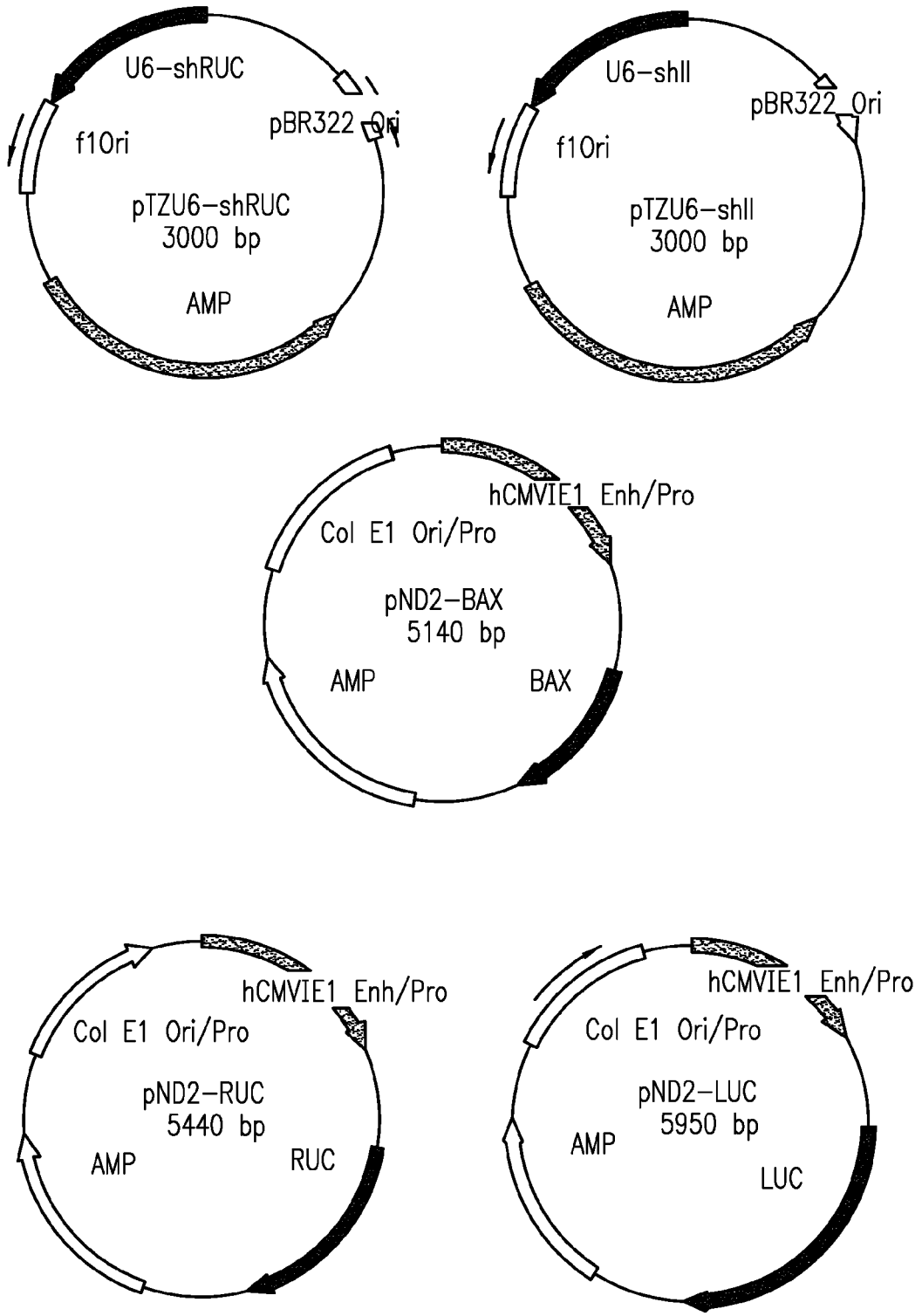
FIG. 1 shows schematic depictions of the plasmids used to generate mammalian cells containing an RNAi molecule (shRUC and shII) and/or to generate ACs (BAX), as well as plasmids containing reporter genes (RUC and LUC) used to monitor the downregulation of a target gene (RUC) in accordance with a method of the present invention.

According to one embodiment of the present invention, there is provided a method for generating an apoptotic cell (AC) that contains an interfering RNA (RNAi) molecule capable of down regulating a chosen target gene. According to another embodiment of the present invention, there is provided method for delivering the RNAi molecule to a mammalian cell expressing the target gene using the AC. According to another embodiment of the present invention, there is provided a mammalian host cell containing an RNAi molecule and a vector capable of expressing a pro-apoptotic protein.

As used in this disclosure, except where the context requires otherwise, the term "comprise" and variations of the term, such as "comprising," "comprises" and "comprised" are not intended to exclude other additives, components, integers or steps.

As used in this disclosure, the term "substantially complementary" and variations of the term, such as "substantial complement," means that at least 90% of all of the consecutive residues in a first strand are complementary to a series of consecutive residues of the same length of a second strand. As will be understood by those with skill in the art with reference to this disclosure, one strand can be shorter than the other strand and still be substantially complementary. With respect to the invention disclosed in this disclosure, for example, the RNAi, siRNA or shRNA can be shorter or longer than the complementary messenger RNA (mRNA) for the target gene interest; however, it is preferable that the RNAi molecule is shorter than and substantially complementary to its corresponding mRNA.

One step of the method is providing an RNAi molecule directed to a target gene of interest.

"RNAi molecule" refers to a nucleic acid that forms a double stranded RNA, which double stranded RNA has the ability to reduce or inhibit expression of a gene or target gene when the RNAi molecule present in the same cell as the gene or target gene. In general, RNAi molecules are fragments of double-stranded RNA (dsRNA), which share a homologous sequence with a target gene. The dsRNA of an RNAi molecule typically contains a "sense" sequence corresponding a partial sequence of the target gene messenger RNA (mRNA) and an "antisense" sequence that is substantially complementary and capable of specifically hybridizing to a target gene mRNA.

RNAi molecules include small interfering RNAs (siRNAs), which are comprised of short dsRNA molecules. In one embodiment, a siRNA comprises a dsRNA containing an antisense sequence substantially or completely complementary to a target gene mRNA. The portions of the siRNA that hybridize to form the dsRNA are typically substantially or completely complementary to each other. The sequences of the siRNA can correspond to the full length target gene, or a subsequence thereof. Typically, the siRNA is at least about 15-50 nucleotides in length (e.g., each complementary sequence of the double stranded siRNA is 15-50 nucleotides in length, and the double stranded siRNA is about 15-50 base pairs in length), preferably about 19-27 base pairs in length, e.g., 19, 20, 21, 22, 23, 24, 25, 26 or 27 nucleotides in length.

In a preferred embodiment, the double stranded portion of the siRNA is about 19-23 base pairs and contains two-base single-stranded overhangs on each end, mimicking the product naturally produced by the endoribonuclease Dicer in vivo. Suitable siRNAs are integrated into a multiprotein complex called the RNA-induced silencing complex (RISC), which initiates the degradation of homologous mRNA.

Synthesis of the siRNA can readily be accomplished by phosphoramidite chemistry and can be obtained from a number of commercial sources well known in the art, as will be understood by those with skill in the art with reference to this disclosure.

An alternative to individual chemical synthesis of siRNA is to construct a sequence for insertion in an expression vector. Several RNAi vectors for the transcription of inserts are commercially available (e.g., Ambion, Austin, Tex.; Invitrogen, Carlsbad, Calif.). Some use an RNA polymerase III (Pol III) promoter to drive expression of both the sense and antisense strands separately, which then hybridize in vivo to make the siRNA. Other vectors are based on the use of Pol III to drive expression of short "hairpin" RNAs (shRNA), individual transcripts that adopt stem-loop structures, which are processed into siRNAs by the RNAi machinery. An example of an RNAi vector is the pTZU6 vector shown in FIG. 1.

Accordingly, RNAi molecules also include short "hairpin" RNA (shRNA), which functions in a similar manner as siRNA. Whereas siRNA is comprised of two strands of complementary RNA that can be synthesized, a shRNA is encoded by DNA as a single RNA molecule that hybridizes to itself with a loop at one end. The "hairpin" loop of the shRNA is cleaved intracellularly yielding a molecule similar to a siRNA.

A typical shRNA vector design incorporates two inverted repeats, containing the sense and antisense target sequences, separated by a loop sequence. Commonly used loop sequences contain 8-9 bases. A terminator sequence consisting of 5-6 poly dTs may be present at the 3' end and cloning sequences can be added to the 5' ends of the complementary oligonucleotides. Referring to FIG. 1, two specific inserts encoding are shown, shRUC and shII, which encode shRNAs. The polynucleotide sequences for these inserts are SEQ ID NO:1 and SEQ ID NO:2.

Any gene expressed within living cells, which are capable of phagocytosis and uptake of apoptotic cells, can be selected as the target gene. For example, one could deliver plasmid DNA that expresses a RNAi molecule that regulates immunity, e.g., by downregulation of CD40 expression to induce tolerance. One or several RNAi molecules can be designed to downregulate the expression of one or several chosen target genes in living cells following a routinely used method, such as computer software or random selection of target sequence within the messenger RNA of the target gene followed by experimental determination of target RNA degradation.

Downregulation is the process by which a cell decreases the number of a cellular component, such as RNA or protein in response to external variable. RNAi down regulates a gene function by mRNA degradation. Thus, the degree of RNA interference achieved is directly proportional to the level of mature mRNA and the translated proteins. The terms "downregulate," "downregulation," "downregulating" or "downregulated" interchangeably refer to a protein or nucleic acid (RNA) that is transcribed or translated at a detectably lower level, in comparison to a normal or untreated cell. Downregulation can be detected using conventional techniques for detecting and/or measuring target mRNA (i.e., RT-PCR, PCR, hybridization) or target proteins (i.e., ELISA, immunohistochemical techniques, enzyme activity). Downregulation can be 10%, 20%, 30%, 40%, 50%, 60%, 70%, 80%, 90% etc. in comparison to a normal or untreated cell. In certain instances, downregulation is 1-fold, 2-fold, 3-fold, 4-fold or more lower levels of transcription or translation in comparison to a normal or untreated cell.

Another step of the method is introducing an RNAi molecule into a cell, which has not undergone apoptosis, i.e., a pre-apoptotic cell (pre-AC). Any mammalian cell can be used because they can be all induced to undergo apoptosis and are capable of carrying out RNAi reactions. The RNAi molecules are delivered into living cells that will be made apoptotic either in vitro or directly in vivo, depending on the desired application.

In one embodiment the pre-ACs express known or unknown antigens capable of eliciting an immune response. For example, the specific antigen may be autoantigen that is recognized by the immune system of patients suffering from a specific autoimmune disease.

The RNAi molecules can be delivered directly as RNA by transfecting cells with short interfering RNAs (siRNAs) using electroporation or other accepted methods described in the literature. For example, delivery of siRNA directly in cells can be achieved by using microinjection or the use of transfection reagent specialized for siRNA-delivery.

Alternatively, the preferred method is to deliver a DNA expression vector encoding a short hairpin RNA (shRNA) that functions as a RNAi molecule, delivered via electroporation, cationic- or liposome-mediated transfection, viral delivery, or direct injection. This approach permits higher concentrations of RNAi molecules in ACs.

After introducing the RNAi molecule into the pre-apoptotic cell, the next step of the method is inducing apoptosis, thereby creating an AC containing the RNAi molecule As will be appreciated by one of skill in the art, apoptosis is a form of cell death in which a programmed sequence of events leads to the elimination of cells without releasing harmful substances into the surrounding area. Apoptosis plays a crucial role in developing and maintaining health by eliminating old cells, unnecessary cells, and unhealthy cells. The human body replaces perhaps a million cells a second. Apoptosis is also called programmed cell death or cell suicide. Strictly speaking, the term apoptosis refers only to the structural changes cells go through, and programmed cell death refers to the complete underlying process, but the terms are often used interchangeably.

Morphological features associated with cells undergoing apoptosis include, membrane blebbing, aggregation of chromatin at the nuclear membrane, shrinking of the cytoplasm and condensation of the nucleus, fragmentation of the cell into smaller bodies, formation of apoptotic bodies, and pore formation in the mitochondrial membrane, involving proteins of the bcl-2 family. Biochemical features associated with the energy (ATP)-dependent process of programmed cell death include non-random mono- and oligonucleosomal length fragmentation of DNA (ladder pattern after agarose gel electrophoresis), release of cytochrome c, apoptosis-inducing factor (AIF) and other factors into the cytoplasm by mitochondria, activation of the caspase cascade, and alterations in membrane biochemistry (i.e. translocation of phosphatidylserine from the cytoplasmic to the extracellular side of the membrane).

Apoptosis can be induced experimentally by exposing cells to various stimuli, including chemicals or radiation. Topoisomerase inhibitors such as etoposide (also known as VP-16) are potent inducers of apoptosis, and are widely used in the study of programmed cell death. Alternatively, cells transfected in vitro can be made apoptotic using exposure to ultra violet light or co-delivery of a gene or cDNA coding for a pro-apoptotic protein, for example, the BAX protein. For UV induced apoptosis, cells are simply exposed to UV-B light for 10 min at a distance of 10 cm. For BAX-induced apoptosis, delivery and expression of the cDNA into cells is sufficient to trigger apoptosis.

In one embodiment, the method includes the further step of introducing a plasmid DNA or viral expression vector containing a polynucleotide sequence encoding a pro-apoptotic protein into the mammalian cells. With reference to FIG. 1, there is shown a map for such vector, pND2-BAX, wherein expression of the BAX cDNA is under the control of the hCMV IE1 enhancer/promoter. The polynucleotide sequence encoding the BAX protein is set forth in SEQ ID NO:3.

Cells can be transfected in vitro, made apoptotic and then injected into a patient, preferably intravenously. A similar approach can be used to generate ACs containing RNAi molecules in vivo. In this case the preferred approach is to deliver plasmid DNA coding for shRNA of choice as well as a pro-apoptotic protein. The DNA can be delivered into a chosen organ or tissue, using electroporation, gene-gun, or injection.

In one embodiment the invention further provides a method of transfecting mammalian cells by exposing a live cell containing a target gene to an AC containing an RNAi molecule directed to the target gene so that the RNAi molecule downregulates expression of the target gene.

The live mammalian cells can be cell lines grown in vitro, or cells of any given tissue in a living body in vivo. Living cells expressing one or several genes targeted by the RNAi molecule gene are exposed to the ACs containing the RNAi molecule. Any endogenous or exogenous gene expressed within living cells can be the target of the RNAi molecule. Expression of an exogenous gene can be accomplished by introduction of an expression vector containing a polynucleotide encoding a target gene of interest. Again, these cells can be cells grown in vitro or can be cells of any tissue in vivo.

The in vitro experiments disclosed herein demonstrate that RNAi molecules present in ACs can transfect living cells with the RNAi molecules. The ACs are phagocytosed and processed by the living cells, and the RNAi molecules that were present in the ACs downregulate the expression of the target gene(s) in living cells.

Most cells have some phagocytic ability, however, the two most important cell types whose major function is phagocytosis are polymorphonuclear leukocytes and the monocyte-macrophage lineage cells (monocytes, macrophages, Kupffer cells, Langerhans cells, dendritic cells, and glial cells). As will be appreciated by one of skill in the art, phagocytosis of ACs occurs constantly in vivo to remove dead cells. Accordingly, it is expected that phagocytosis and uptake of ACs containing RNAi molecules will also occur in vivo, as has been shown for ACs carrying genomic DNA. (Holmgren et al, 1999, Blood vol 11 p 3956)

Many cells can process ACs, in particular, antigen-presenting APCs, like DCs, that direct immune responses. An antigen-presenting cell (APC) is a cell that displays foreign antigen complexed with MHC on its surface. T-cells may recognize this complex using their T-cell receptor (TCR). Although almost every cell in the body is technically an APC, since it can present antigen to CD8+ T cells via MHC class I molecules, the term is often limited to those specialized cells that can prime T cells (i.e., activate a T cell that has not been exposed to antigen). These cells generally express MHC class II as well as MHC class I molecules, and can stimulate CD4+ ("helper") cells as well as CD8+ ("cytotoxic") T cells. Traditional antigen-presenting cells include macrophages; dendritic cells; Langerhans cells; and B-lymphocytes. Other cells, like fibroblasts (skin), thymic epithelial cells, thyroid epithelial cells, glial cells (brain), pancreatic beta cells and vascular endothelial cells, can be stimulated by certain cytokines such as IFN-γ, to express the major histocompatibility complex proteins required for interaction with naive T cells.

A significant advantage of AC-mediated transfection of APCs with RNAi molecules is that it will permit the co-delivery of any and all antigens present in ACs together with one or possibly several selected RNAi molecules to the same APCs. In addition, AC-mediated transfection is a physiological means of delivering RNAi that could result in a high number of transfected cells, because ACs are rapidly phagocytosed and recruit APCs in vivo.

The ability to deliver antigen and a RNAi molecule capable of modifying the function of APCs, like DCs, as part of the same package permits increased control over induced immune responses (i.e., tolerogenic vs immunogenic) for antigens present in ACs. Important applications for this approach include the prevention of transplant rejection (with donor antigens) and treatment of autoimmune diseases (with autoantigens).

The clinical potential applications of this approach are multiple, and include any situation where a gene must be downregulated for therapeutic purposes. The approach is particularly well-suited for manipulation of immune responses because antigen-presenting cells are very efficient at taking in and processing ACs. The ability to deliver antigen(s) and RNAi molecules as a single package means that a specific dendritic cell will mount an immune response directed by the RNAi molecules to the antigen(s) of the ACs. For example, if one wishes to induce tolerance or immunity to a specific antigen, one could deliver plasmid DNA coding the antigen, a RNAi molecule that regulates immunity, for example downregulation of CD40 expression to induce tolerance, and a pro-apoptotic protein. Such ACs would be processed by APCs which would be more likely to trigger tolerance for the antigen(s) carried by ACs.

The invention provides for the generation of mammalian ACs containing a chosen RNAi molecule that downregulates the expression of a chosen target gene. The ACs can be generated using UV or a pro-apoptotic cDNA like that coding for the BAX protein. The invention may be appreciated in certain aspects with reference to the following examples, offered by way of illustration, not by way of limitation. Materials, reagents and the like to which reference is made in the following examples are obtainable from commercial sources, unless otherwise noted.

FIG. 1 shows schematic depictions of the plasmids used to generate mammalian cells containing an RNAi molecule (shRUC and shII) and/or to generate ACs (BAX), as well as plasmids containing reporter genes (RUC and LUC) used to monitor the downregulation of a target gene (RUC) in accordance with a method of the present invention. The plasmid maps were prepared using Plasmid Processor W software (T. Kivirauma, P. Oikari and J. Saarela, Dept. of Biochemistry & Biotechnology, U. of Kuopio, plasmid@uku.fi.

Referring to FIG. 1, the sequence of shRUC for *Renilla* luciferase site C introduced into the pTZU6-shRUC plasmid is SEQ ID NO:1. The sequence of shII for HIV-1 rev (site II) introduced into the pTZU6-shII plasmid is SEQ ID NO:2. The sequence of BAX for human BAX inserted into the pND2-BAX plasmid is SEQ ID NO:3. The sequence of LUC for Firefly luciferase inserted into the pND2-LUC plasmid is SEQ ID NO:4. The sequence of RUC for *Renilla* luciferase introduced into the pND2-RUC plasmid is SEQ ID NO:5.

Figure 2:
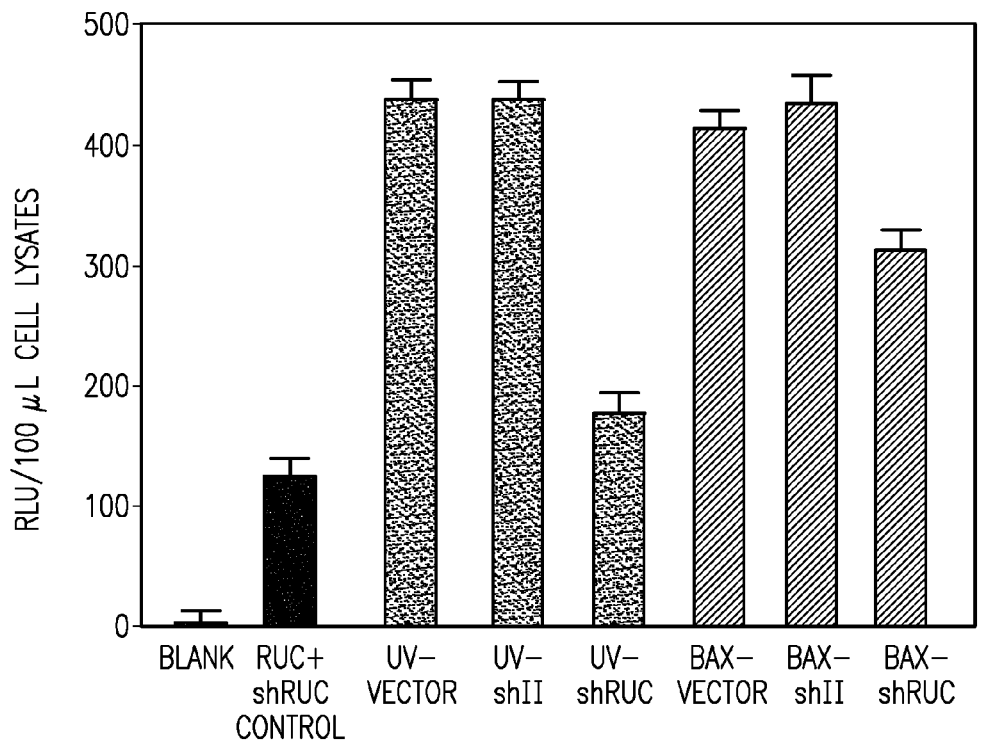
FIG. 2 shows *Renilla* luciferase (RUC) activity from COS-7 cells expressing the RUC cDNA and co-cultured with differently treated COS-7 ACs.

As an example, FIG. 2 shows the effect of ACs containing a short hairpin RNA (shRUC) that causes degradation of the *Renilla* luciferase mRNA. Simian COS-7 cells expressing *Renilla* luciferase cDNA were incubated with UV- or BAX-induced apoptotic COS-7 cells containing shRUC, and *Renilla* luciferase activity was measured.

COS-7 cells were transfected with 5 µg RUC plasmid DNA coding for *Renilla* luciferase to measure effects of ACs and 2 µg LUC plasmid DNA coding for firefly luciferase for normalization. Differently treated COS-7 cells were made apoptotic and added to the live COS-7 cells 3 hours after the live cells had been transfected with luciferase. UV- and BAX-induced apoptosis yielded ~80% and ~30% ACs, respectively. The ratio of cells induced to be apoptotic added to living cells expressing luciferase cDNA was 2:1. Cells were then harvested after 20 hours culture to measure luciferase activities. Staining of live and apoptotic COS-7 cells showed uptake of ACs by live cells (data not shown).

All transfections were performed using Superfect (Qiagen, Valencia, Calif.). Measurements were performed in triplicate from 2 separate experiments.

FIG. 2 shows *Renilla* luciferase (RUC) activity from COS-7 cells expressing the RUC cDNA and co-cultured with differently treated COS-7 ACs. Referring now to FIG. 2: Blank shows background luminescence activity from untransfected cells; RUC+shRUC control: shows RUC activity when cells were co-transfected with luciferase plasmids (5 µg RUC, 2 µg LUC) and plasmid encoding shRUC (10 µg) to confirm downregulating activity of shRUC (no ACs added); UV-Vector shows RUC activity when added ACs were generated by transfecting COS-7 cells with 10 µg plasmid vector alone and UV exposure 48 hrs post transfection; UV-shII shows RUC activity when the pre-ACs were transfected with 10 µg plasmid DNA encoding a shRNA targeting the HIV virus II gene as negative control and made apoptotic as described for UV-AC vector; UV-AC shRUC shows RUC activity when the pre-ACs were transfected with 10 pg plasmid DNA encoding a shRNA targeting the RUC cDNA and made apoptotic as described for UV-AC vector; BAX-vector shows RUC activity when the pre-ACs were co-transfected with plasmid DNA coding for BAX (10 µg) and plasmid vector alone (10 µg) and ACs were harvested 30 hrs post transfection (no UV-treatment); BAX-shII shows RUC activity when the pre-ACs were transfected with plasmid DNA coding for BAX and control shRNA and processed as described for BAX-vector; and BAX-shRUC shows RUC activity when the pre-ACs were transfected with plasmid DNA coding for BAX and shRUC and processed as described for BAX-vector.

These results show ACs containing shRUC decreased luciferase activity in live cells expressing an RUC target gene. In contrast, co-cultivation with ACs containing a control shRNA (shII) targeting the HIV-1 rev gene did not. Addition of ACs containing vector alone did not affect *Renilla* luciferase activity (data not shown).

Figure 3:
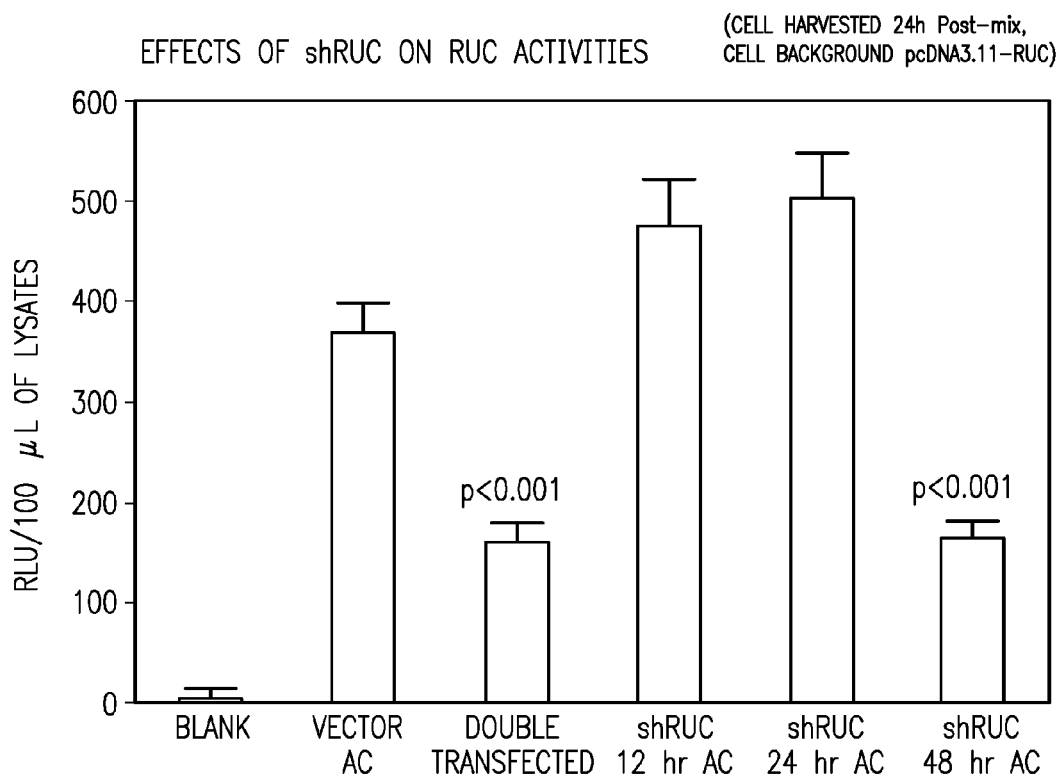
FIG. 3 shows the effects of duration of expression of shRUC prior to induction of apoptosis on *Renilla* luciferase activity in live cells.

FIG. 3 shows the effects of duration of expression of shRUC prior to induction of apoptosis of shRUC-containing cells on *Renilla* luciferase activity in live cells. The data indicate that ACs containing shRUC that had been expressed for 12 and 24 hrs did not downregulate activity of luciferase after incubating the apopotic and live cells. Expression of shRUC for 48 hrs was necessary to observe loss of luciferase actvity. These data indicate that the loss of luciferase activity after adding ACs containing shRUC was not due to shRUC plasmid contamination into cells expressing RUC luciferase cDNA, but to expression of shRUC contained by ACs.

Figure 4:
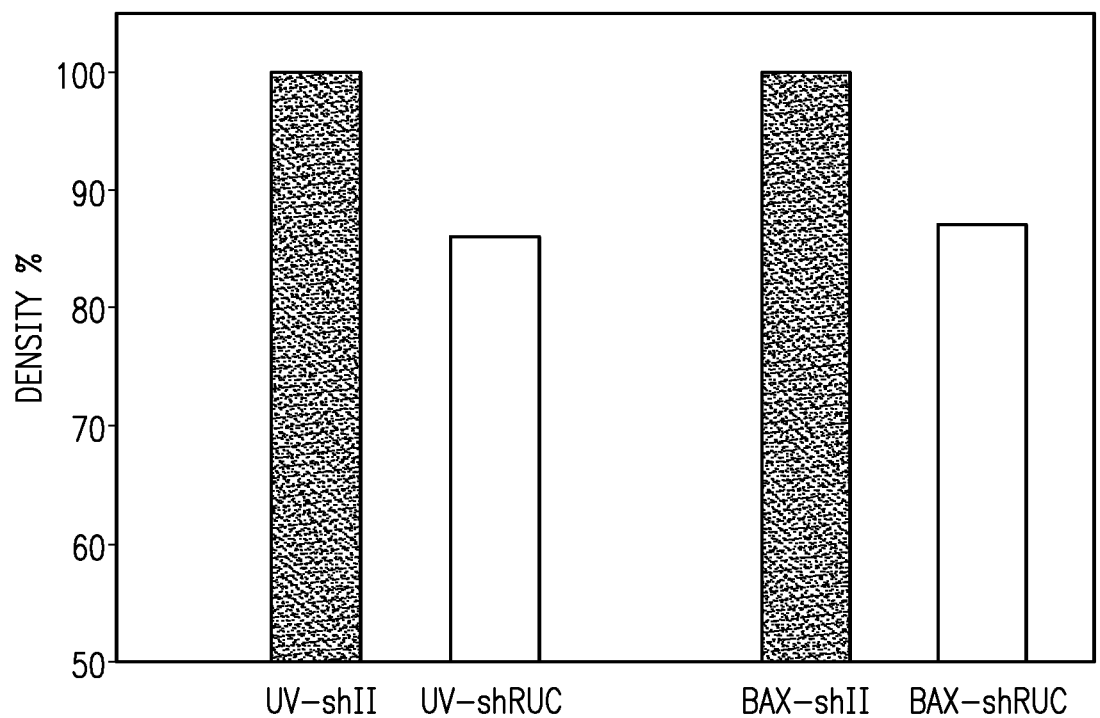
FIG. 4 shows the effects of UV- and BAX-induced ACs containing shRUC on RUC mRNA levels expressed by live cells.

FIG. 4 shows the effects of UV- and BAX-induced ACs containing shII or shRUC on levels of *Renilla* luciferase mRNA in live cells exposed to the AC. Live COS-7 cells transfected with luciferase cDNA were co-cultured with COS-7 ACs containing control shRNA (shII) or shRNA targeting RUC mRNA (shRNA), and induced with UV or BAX, as described for FIG. 2. Total RNA was isolated and semi-quantitative RT-PCR was performed with 100, 200 and 400 ng total RNA template using primers for RUC and the housekeeping gene GAPD-H. Products were separated using agarose gel electrophoresis and cDNA band densities were determined. RUC cDNA amount was normalized for GAPD-H cDNA amount when comparing shII and shRUC treatments for a given method of apoptosis induction. Data is shown as percentage of RUC cDNA found in shRUC-treated cells compared to shII-treated cells.

These results show that shRUC contained by ACs decreased RUC mRNA levels in live cells exposed to the ACs.

All references cited in this disclosure are incorporated herein by reference in their entirety.

REFERENCES

Behlke, M. A. (2006) Progress Towards In Vivo Use of siRNAs. Molecular Therapy 13/4:644-670

Holmgren, L, Szeles, A., Rajnavolgyi, E., Foldman, J., Klein, G., Ernberg, I. and Falk, K. I. (1999) Horizontal Transfer of DNA by the Uptake of Apoptotic Bodies, Blood 93/11: 3956-3963.

Li, M., Qian, H., Ichim, T. M., Ge, W-W., Popov, I. A., Rycerz, K., Neu, J., White, D., Zhong, R., and Min, W.-P. (2004) Induction of RNA Interference in Dendritic Cells. Immunologic Research 30/2:215-230.

Zhao H.-F., L'Abbé D., Jolicoeur, N., Wu, M,. Li, Z., Zhenbao, Y., and Shen S-H. (2005) High-Throughput Screening of Effective siRNAs from RNAi Libraries Delivered via Bacterial Invasion, Nature Methods 2/12:967-973.

What is claimed is:

1. A method of transfecting a mammalian cell comprising:
   (a) providing a mammalian cell expressing a target gene, wherein the mammalian cell is living and capable of phagocytosis; and
   (b) exposing the living mammalian cell to an apoptotic cell, wherein the apoptotic cell comprises an RNAi molecule, and wherein said RNAi molecule is transferred to said living mammalian cell from said apoptotic cell and downregulates the target gene in said mammalian cell.

2. The method of claim 1, wherein the living mammalian cell is a polymorphonuclear leukocyte, a monocyte, a macrophage, a Kupffer cell, a Langerhans cell, a dendritic cell, or a glial cell.

3. The method of claim 1, wherein the mammalian cell is an antigen presenting cell.

4. The method of claim 1, wherein the living mammalian cell is exposed to the apoptotic cell in vivo or in vitro.

5. The method of claim 1 wherein the living mammalian cell expressing the target gene is a first mammalian cell, and the apoptotic cell comprising an RNAi molecule is generated by a method comprising:
   (a) providing an RNAi molecule, wherein the RNAi molecule is capable of downregulating the target gene of interest;
   (b) introducing the RNAi molecule into a second mammalian cell, wherein the second mammalian cell is not the same as the first mammalian cell; and
   (c) inducing apoptosis in the second cell to create an apoptotic cell comprising the RNAi molecule.

6. The method of claim 1 wherein the RNAi molecule is a short interfering RNA (siRNA) or a short hairpin RNA (shRNA).

7. The method of claim 1, wherein the RNAi molecule comprises a polynucleotide sequence substantially complementary to a messenger RNA (mRNA) encoded by the target gene.

8. The method of claim 1, wherein the RNAi molecule comprises a double-stranded RNA (dsRNA) region, which comprises a sense sequence corresponding to a partial sequence of the target gene mRNA, and an antisense sequence that is substantially complementary and capable of specifically hybridizing to the target gene mRNA.

9. The method of claim 1, wherein the RNAi molecule comprises a short double-stranded RNA (dsRNA) region of about 19-27 base pairs.

10. The method of claim 6, wherein the siRNA comprises a short double-stranded RNA (dsRNA) region of about 19-23 base pairs, and wherein the siRNA further comprises a single-stranded overhang of about two nucleotides on one end of each strand.

11. The method of claim 5, wherein the RNAi molecule is provided by a vector capable of expressing a short hairpin RNA (shRNA) or a short interfering RNA (siRNA).

12. The method of claim 11, wherein the vector comprises one or more than one RNA polymerase III promoter sequences controlling transcription of the RNAi molecule.

13. The method of claim 5, wherein the RNAi molecule is introduced into the second mammalian cell by transfection, electroporation or microinjection.

14. The method of claim 5, wherein the RNAi molecule is introduced into the second mammalian cell by delivering a DNA plasmid or viral vector encoding a short hairpin RNA (shRNA).

15. The method of claim 5, wherein apoptosis is induced by exposing the second mammalian cell comprising the RNAi molecule to ultraviolet light.

16. The method of claim 5, wherein apoptosis is induced by expression of a pro-apoptotic protein.

17. The method of claim 5, further comprising introducing a plasmid DNA or viral expression vector comprising a polynucleotide sequence encoding a pro-apoptotic protein into the second mammalian cell.

18. The method of claim 17, wherein the pro-apoptotic protein is BAX protein.

19. The method of claim 5, wherein the RNAi molecule is introduced into the mammalian cell and apoptosis is induced in vitro.

20. The method of claim 17, wherein the RNAi molecule and the expression vector comprising a polynucleotide sequence encoding a pro-apoptotic protein are introduced into the mammalian cell by co-transfection.

21. The method of claim 17, further comprising introducing into an organ or tissue the RNAi molecule and the expression vector comprising a polynucleotide sequence encoding a pro-apoptotic protein by electroporation, gene-gun, or injection.

22. The method of claim 1, wherein the apoptotic cell further comprises an antigen.

23. The method of claim 22, wherein the antigen is an autoantigen and a donor antigen.

24. The method of claim 11, wherein said vector does not comprise a nucleotide sequence that mediates homologous recombination in a mammalian cell.

25. The method of claim 14, wherein said DNA plasmid or viral vector does not comprise a nucleotide sequence that mediates homologous recombination in a mammalian cell.

* * * * *

SEQUENCE LISTING

```
<160> NUMBER OF SEQ ID NOS: 5

<210> SEQ ID NO 1
<211> LENGTH: 62
<212> TYPE: DNA
<213> ORGANISM: Artificial
<220> FEATURE:
<223> OTHER INFORMATION: Synthetic
<220> FEATURE:
<221> NAME/KEY: source
<222> LOCATION: (1)..(62)

<400> SEQUENCE: 1
caccgtagcg cggtgtatta taccagtgtg ctgtcctggt ataatacacc gcgctactttt      60 tt                                                                      62

<210> SEQ ID NO 2
<211> LENGTH: 56
<212> TYPE: DNA
<213> ORGANISM: Artificial
<220> FEATURE:
<223> OTHER INFORMATION: Synthetic
<220> FEATURE:
<221> NAME/KEY: source
<222> LOCATION: (1)..(56)

<400> SEQUENCE: 2
gcctgtgcct cttcagctac cgaagcttgg gtagctgaag aggcacaggc tttttt           56
```

<210> SEQ ID NO 3
<211> LENGTH: 577
<212> TYPE: DNA
<213> ORGANISM: Homo sapiens

<400> SEQUENCE: 3

| | | | | | |
|---|---|---|---|---|---|
| atggacgggt | ccggggagca | gcccagaggc | gggggggccca | ccagctctga | gcagtcatga | 60 |
| agacaggggc | ccttttgctt | cagggtttca | tccaggatcg | agcagggcga | aggggggga | 120 |
| ggcacccgag | ctggccctgg | acccggtgcc | tcaggatgcg | tccaccaaga | agctgagcga | 180 |
| gtgtctcaag | cgcatcgggg | acgaactgga | cagtaacatg | gagctgcaga | ggatgattgc | 240 |
| cgccgtggac | acagactccc | cccgagaggt | cttttttccga | gtggcagctg | acatgttttc | 300 |
| tgacggcaac | ttcaactggg | gccgggttgt | cgcccttttc | tactttgcca | gcaaactggt | 360 |
| gctcaaggcc | ctgtgcacca | aggtgccgga | actgatcaga | accatcatgg | gctggacatt | 420 |
| ggacttcctc | cggagcggc | tgttgggctg | gatccaagac | cagggtggtt | gggacggcct | 480 |
| cctctcctac | tttgggacgc | ccacgtgcca | gaccgtgacc | atctttgtgg | cgggagtgct | 540 |
| caccgcctcg | ctcaccatct | ggaagaagat | gggctga | | | 577 |

<210> SEQ ID NO 4
<211> LENGTH: 1653
<212> TYPE: DNA
<213> ORGANISM: Photinus pyralis

<400> SEQUENCE: 4

| | | | | | |
|---|---|---|---|---|---|
| atggaagacg | ccaaaaacat | aaagaaaggc | ccggcgccat | tctatccgct | ggaagatgga | 60 |
| accgctggag | agcaactgca | taaggctatg | aagagatacg | ccctggttcc | tggaacaatt | 120 |
| gcttttacag | atgcacatat | cgaggtggac | atcacttacg | ctgagtactt | cgaaatgtcc | 180 |
| gttcggttgg | cagaagctat | gaaacgatat | gggctgaata | caaatcacag | aatcgtcgta | 240 |
| tgcagtgaaa | actctcttca | attctttatg | ccggtgttgg | gcgcgttatt | tatcggagtt | 300 |
| gcagttgcgc | ccgcgaacga | catttataat | gaacgtgaat | tgctcaacag | tatgggcatt | 360 |
| tcgcagccta | ccgtggtgtt | cgtttccaaa | aaggggttgc | aaaaaatttt | gaacgtgcaa | 420 |
| aaaaagctcc | caatcatcca | aaaaattatt | atcatggatt | ctaaaacgga | ttaccaggga | 480 |
| tttcagtcga | tgtacacgtt | cgtcacatct | catctacctc | ccggttttaa | tgaatacgat | 540 |
| tttgtgccag | agtccttcga | tagggacaag | acaattgcac | tgatcatgaa | ctcctctgga | 600 |
| tctactggtc | tgcctaaagg | tgtcgctctg | cctcatagaa | ctgcctgcgt | gagattctcg | 660 |
| catgccagag | atcctatttt | tggcaatcaa | atcattccgg | atactgcgat | tttaagtgtt | 720 |
| gttccattcc | atcacggttt | tggaatgttt | actacactcg | gatatttgat | atgtggattt | 780 |
| cgagtcgtct | taatgtatag | atttgaagaa | gagctgtttc | tgaggagcct | tcaggattac | 840 |
| aagattcaaa | gtgcgctgct | ggtgccaacc | ctattctcct | tcttcgccaa | aagcactctg | 900 |
| attgacaaat | acgatttatc | taatttacac | gaaattgctt | ctgtggcgc | tcccctctct | 960 |
| aaggaagtcg | gggaagcggt | tgccaagagg | ttccatctgc | caggtatcag | gcaaggatat | 1020 |
| gggctcactg | agactacatc | agctattctg | attacacccg | agggggatga | taaaccgggc | 1080 |
| gcggtcggta | aagttgttcc | attttttgaa | gcgaaggttg | tggatctgga | taccgggaaa | 1140 |
| acgctgggcg | ttaatcaaag | aggcgaactg | tgtgtgagag | gtcctatgat | tatgtccggt | 1200 |
| tatgtaaaca | atccggaagc | gaccaacgcc | ttgattgaca | aggatggatg | gctacattct | 1260 |
| ggagacatag | cttactggga | cgaagacgaa | cacttcttca | tcgttgaccg | cctgaagtct | 1320 |
| ctgattaagt | acaaaggcta | tcaggtggct | cccgctgaat | tggaatccat | cttgctccaa | 1380 |

-continued

```
caccccaaca tcttcgacgc aggtgtcgca ggtcttcccg acgatgacgc cggtgaactt    1440
cccgccgccg ttgttgtttt ggagcacgga aagacgatga cggaaaaaga gatcgtggat    1500
tacgtcgcca gtcaagtaac aaccgcgaaa aagttgcgcg gaggagttgt gtttgtggac    1560
gaagtaccga aaggtcttac cggaaaactc gacgcaagaa aaatcagaga gatcctcata    1620
aaggccaaga agggcggaaa gatcgccgtg taa                                 1653

<210> SEQ ID NO 5
<211> LENGTH: 936
<212> TYPE: DNA
<213> ORGANISM: Renilla reniformis

<400> SEQUENCE: 5
atgacttcga aagtttatga tccagaacaa aggaaacgga tgataactgg tccgcagtgg      60
tgggccagat gtaaacaaat gaatgttctt gattcattta ttaattatta tgattcagaa     120
aaacatgcag aaaatgctgt tattttttta catggtaacg cggcctcttc ttatttatgg     180
cgacatgttg tgccacatat tgagccagta gcgcggtgta ttataccaga tcttattggt     240
atgggcaaat caggcaaatc tggtaatggt tcttataggt tacttgatca ttacaaatat     300
cttactgcat ggtttgaact tcttaattta ccaagaagaa tcattttttgt cggccatgat     360 tggggtgctt gtttggcatt tcattatagc tatgagcatc aagataagat caaagcaata     420
gttcacgctg aaagtgtagt agatgtgatt gaatcatggg atgaatggcc tgatattgaa     480
gaagatattg cgttgatcaa atctgaagaa ggagaaaaaa tggttttgga gaataacttc     540
ttcgtggaaa ccatgttgcc atcaaaaatc atgagaaagt tagaaccaga agaatttgca     600
gcatatcttg aaccattcaa agagaaaggt gaagttcgtc gtccaacatt atcatggcct     660
cgtgaaatcc cgttagtaaa aggtggtaaa cctgacgttg tacaaattgt taggaattat     720
aatgcttatc tacgtgcaag tgatgattta ccaaaaatgt ttattgaatc ggatccagga     780
ttcttttcca atgctattgt tgaaggcgcc aagaagtttc ctaatactga atttgtcaaa     840
gtaaaaggtc ttcatttttc gcaagaagat gcacctgatg aaatgggaaa atatatcaaa     900
tcgttcgttg agcgagttct caaaaatgaa caataa                               936
```